United States Patent [19]

Ragan et al.

[11] Patent Number: 5,125,238
[45] Date of Patent: Jun. 30, 1992

[54] PATIENT WARMING OR COOLING BLANKET

[75] Inventors: Raymond G. Ragan; James G. Stephenson; Charles L. Zuck, all of Marshall, Mich.

[73] Assignee: Progressive Dynamics, Inc., Marshall, Mich.

[21] Appl. No.: 692,572

[22] Filed: Apr. 29, 1991

[51] Int. Cl.⁵ .............................................. A47C 27/08
[52] U.S. Cl. ...................................... 62/259.3; 165/46; 126/204; 128/400; 5/423
[58] Field of Search .............. 62/259.3, 261; 128/400; 165/46; 5/284, 423, 469; 126/204

[56] References Cited

U.S. PATENT DOCUMENTS

| | | | |
|---|---|---|---|
| 1,965,424 | 7/1934 | Mascolo | 128/256 |
| 2,093,834 | 9/1937 | Gaugler | 128/145 |
| 2,110,022 | 3/1938 | Kliesrath | 5/334 |
| 2,601,189 | 6/1952 | Wales, Jr. | 4/160 |
| 3,942,202 | 3/1976 | Chevrolet | 5/348 R |
| 4,026,350 | 5/1977 | Zembrzuski | 165/46 |
| 4,149,541 | 4/1979 | Gammons et al. | 128/400 |
| 4,572,188 | 2/1986 | Augustine et al. | 128/380 |
| 4,777,802 | 10/1988 | Feher | 62/261 X |
| 4,867,230 | 9/1989 | Voss | 165/46 |
| 4,907,308 | 3/1990 | Leininger et al. | 5/455 |

Primary Examiner—Albert J. Makay
Assistant Examiner—William C. Doerrler
Attorney, Agent, or Firm—Beaman & Beaman

[57] ABSTRACT

A disposable patient heating or cooling blanket having three layers of flexible sheeting two of which form an air chamber, the third of which is a comfortable layer for contact with the patient and which, having a greater friction characteristic, aids in keeping the blanket in place on the patient. The patient is bathed in conditioned air through a multiplicity of orifices in the bottom layers of the blanket and the size and location of the orifices are such that sufficient pressure exists within the blanket to prevent crimping blockage and to insure a uniform flow of air through the orifices throughout the blanket area. Conditioned air is introduced horizontally through an external nozzle which is inserted into a low cost foldable fitting plate bonded to the blanket which permits the blanket to be concisely folded and packaged.

9 Claims, 1 Drawing Sheet

PATIENT WARMING OR COOLING BLANKET

BACKGROUND OF THE INVENTION

Medical care providers have long recognized the need to provide warmth and cooling directly to patients as part of their treatment and therapy. The relatively recent proliferation of mobile emergency medical facilities as an adjunct to fire departments and the expansion of clinical facility services in the community has increased the number of sites where such treatments must be given. Consequently, there has evolved a need for an inexpensive disposable patient thermal control blanket which will provide a distributed air flow while maintaining sufficient pressure in the blanket to prevent blockage of the flow due to the blanket folding or crimping.

FIELD OF THE INVENTION

The present application relates to a patient warming or cooling blanket which employs a bath of temperature controlled air applied to the patient rather than utilizing direct or indirect contact with a heat exchanger.

DESCRIPTION OF RELATED ART

Devices of the type described above are well known in the art, for example U.S. Pat. No. 2,093,834 discloses of a mechanism for providing localized air conditioning by means of an inflatable covering constructed of plurality of tubular enclosures of porous material in conjunction with a quilted covering. Devices of this construction rely on a recirculating cooling or heating medium and transfer heat mainly through contact with the blanket surfaces. This patented device as well as those of U.S. Pat. Nos. 2,601,189 and 4,572,188 which are also of such essentially tubular or corrugated construction have the disadvantage that they are longitudinally rigid, relatively uncomfortable, have a high profile, and due to the complexity of devices of this type, they are relatively expensive to construct. U.S. Pat. No. 2,093,834 shows a construction which is susceptible to tube wall compression which constricts the flow path and increases internal pressure resulting in flow restriction and rigidity due to the entrapment of air within the device. The construction of the devices of U.S. Pat. Nos. 2,601,189 and 4,572,188 include lateral passages to adjacent tubes which do not fully alleviate the tube compression flow restriction problem and are more expensive to fabricate than the instant invention by virtue of their complex construction.

OBJECTS OF THE INVENTION

In view of the foregoing shortcomings in pneumatic temperature control patient blanket fabrication, it is an object of the invention to provide a disposable blanket for use in patient warming and cooling applications which is simple to operate, easy to construct, economical to manufacture and concisely storable.

A further object of the invention is to provide a pneumatic blanket which employs materials and structural elements which are comfortable to the patient with whom they contact.

An additional object of the pneumatic patient blanket is to provide an even, pleasant and healthy flow of air uniformly over the covered area regardless of where the blanket air chamber may be compressed.

SUMMARY OF THE INVENTION

The invention pertains to disposable heating and cooling patient blankets. An external air conditioning unit provides low pressure heated or dehumidified and cooled air through a flexible hose having a supply nozzle. Conditioned air is introduced into the blanket pneumatic chamber by means of the supply nozzle which inserts into an inlet port through a low-cost folding cardboard fitting plate mounted on the edge of the blanket.

The folding cardboard fitting plate has a folded storage mode to permit the blanket to be folded into a compact mass for storage. In its open operative mode the fitting plate is essentially planar having an opening which is sized to snugly receive the supply nozzle horizontally through the blanket edge directly into a pneumatic flow chamber thereby avoiding opposite wall obstructions of the supply nozzle airflow.

The pneumatic flow chamber is constructed of, and defined by, the interface of two polyethylene sheets heat bonded together at their perimeters and at a plurality of staking points in a single step of the assembly process. Air flow through the blanket is enhanced by the creation of fully redundant flow paths around the staggered dot staking pattern which is distributed throughout the blanket area. A layer of non-woven wood pulp airlaid material is adhesively bonded to the bottom sheet of polypropylene thereby forming a laminated layer and both the bottom sheet of polyethylene and airlaid material are perforated by an array of selectively sized orifices. The orifices are distributed in a regular pattern throughout the area bounded by the pneumatic chamber parameter and allow the emission of an even, gentle air stream from the blanket bottom and are of such size that the blanket will be pressurized enough to hold its shape and resist crimping of the air flow due to normal compressive forces being applied to the blanket. The airlaid material rests comfortably against the patient bathing the patient in the air emitted from the orifices and helps keep the blanket from sliding off the patient because of its high frictional characteristics.

BRIEF DESCRIPTION OF THE DRAWINGS

In order that the invention may be clearly understood, it will now be described, by way of example, with reference to the accompanying drawings, wherein.

DESCRIPTION OF THE PREFERRED EMBODIMENTS

Figure 2:
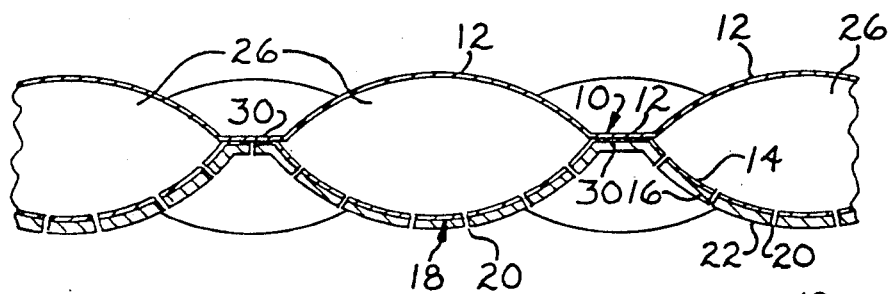
FIG. 2 is an enlarged, cross-sectional, detail elevation view of the blanket showing the pneumatic chamber between staking points as well as the relationship of the several blanket layers in accord with the invention.

In the invention, a three layer construction is employed to form the patient blanket 10 with two layers forming an air chamber and a third layer providing a comfortable surface for contact with the patient. It will be obvious to a person familiar in the art, that any of a number of flexible sheeting materials can be used for the upper flexible sheet 12 and lower flexible sheet 14, but in the preferred embodiment for economy, strength and flexibility considerations 1.5 mil thickness polyethylene sheeting was selected. Simple, economical assembly of the blanket begins when the .015 inch thick layer of non-woven fibrous layer of wood pulp airlaid material 16 is adhesively bonded to the lower side of the 1.5 mil thickness lower flexible sheet 14 forming the laminate assembly 18, as shown in FIG. 2. This fibrous layer 16 provides a comfortable surface in contact with the patient and its high frictional characteristic helps keep the blanket in place on the patient. A material of this type is available under the trademark "AIRTEX" from the Fiberware Corporation. The laminate assembly 18 is then perforated with specifically sized orifice holes 20 by means of a punch plate. The orifice size is determined by the volume flow characteristics of the air source and by the following formula:

$$Q = KA\sqrt{\Delta P}$$

Where Q is the air flow rate in cubic feet per minute, K is a constant, A is the area of the orifices and $\Delta P$ is the differential pressure in inches of water at standard room conditions. From test results it was determined that for proper flow and inflation K should be 11.718, A should equal 0.001 square inches for each square inch of blanket which will produce 0.035 inch diameter orifices on 1 inch centers and $\Delta P$ is 0.25 inches of water.

Figure 1:
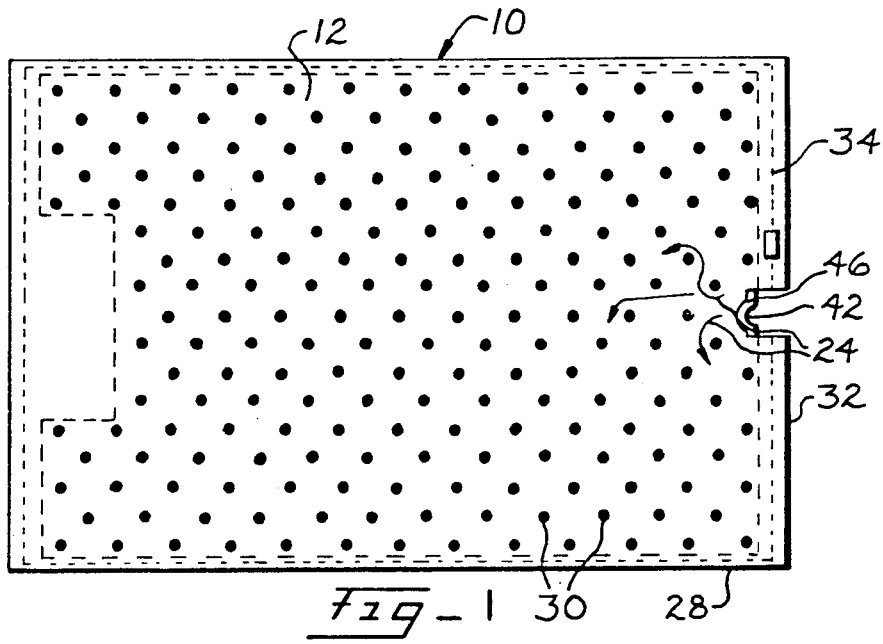
FIG. 1 is a plan view of the patient blanket in accord with the invention.

The sizing of the orifices 20 by this method assures sufficient inflation to minimize crimping of the blanket while providing continuous air flow to the lower surface 22 that is both evenly distributed and above the minimum flow quantity required. The problems associated with compressing or crimping the blanket are also alleviated through the invention's incorporation of a multiplicity of redundant flow paths as shown by the arrows 24 within the pneumatic flow chambers 26 as shown in FIG. 1 due to the inflation of the blanket.

Subsequent to the lower layer lamination and orifice perforation, the upper flexible sheet 12 is laid upon the laminated assembly 18 and the periphery 28 of the two polyethylene layers are heat sealed together. In the same process step, the two flexible sheets are also staked together in a staggered pattern of one inch diameter heat sealed staking bonds or welds 30 throughout the area within the periphery seal. This staking creates the redundant flow paths 24 feature of the invention as well as serving the dual purposes of reducing stresses to the inflated structure through reducing the radius of the chambers 26, and through the same mechanism reducing the blanket inflated thickness while assuring flow distribution and continuity across the lower surface 22 of the blanket.

The preferred air inlet location is through a fitting plate on the blanket edge 32 intermediate the upper flexible sheet first end 34 and the lower flexible sheet first end 36. In this blanket edge center, a semicircular cut is made through the laminated assembly 18 and the upper flexible sheet 12. When the blanket is inflated, these semicircular cuts form an essentially horizontal circular air inlet port 42. By horizontal insertion of an air supply nozzle through the fitting plate into the blanket air flow is unrestricted by blanket film members pressing against the nozzle opening, and furthermore, there is no need to support the nozzle's weight. The conditioned air is introduced through a flexible hose 44 having a frustoconical end nozzle 38 converging towards the nozzle end 40.

Figures 3, 4, 5:
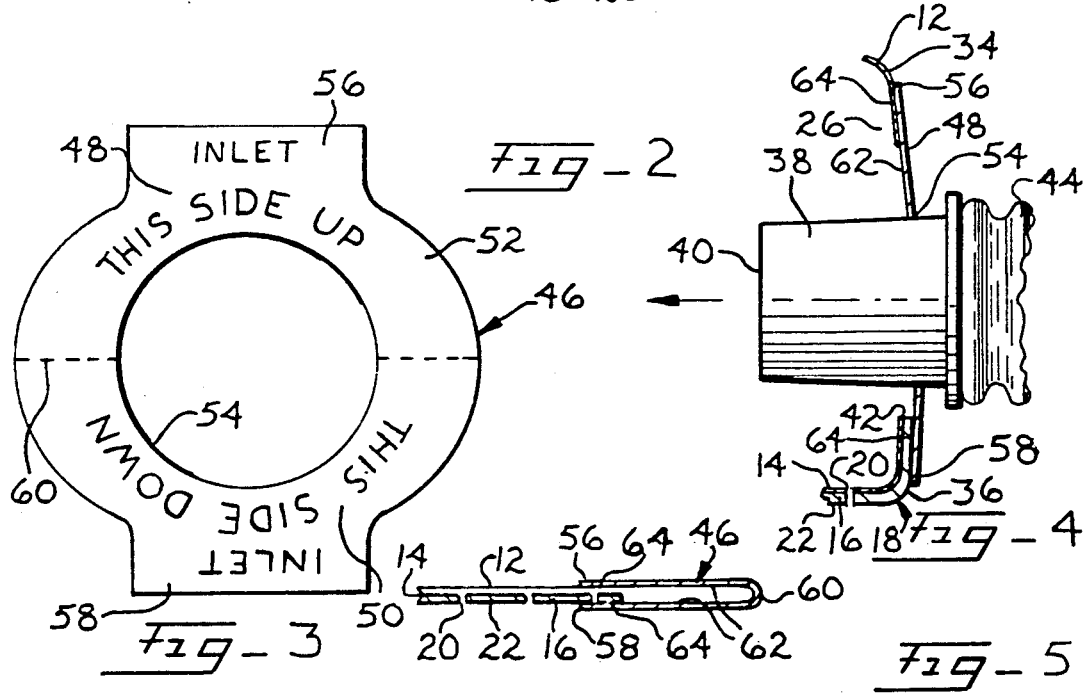
FIG. 3 is an elevational view of the folding cardboard fitting plate in accord with the invention shown in the open or unfolded mode.
FIG. 4 is an enlarged, elevational, detail sectional view of the folding cardboard fitting plate air inlet connection with an external air supply nozzle inserted therein in accord with the invention.
FIG. 5 is an enlarged, elevational, detail view of the cardboard fitting plate as attached to the blanket in accord with the invention and shown in the folded storage condition.

The fitting plate 46, in accord with the invention, is best shown in FIGS. 3, 4 and 5. The plate 46 is fabricated of a low cost, foldable material with an exterior surface suitable for direct labeling. In the preferred embodiment, cardboard was selected as meeting the aforementioned criteria as well as being an inexpensive and easy to print material. The fitting plate 46 is an elongated member having a first end 48 and a second end 50 each with an extension and having a circular central portion 52 intermediate the ends. The circular center portion 52 defines an opening 54 which aligns with the blanket chamber port 42 to snugly receive the frustoconical air supply nozzle 38, thereby introducing conditioned air into the pneumatic flow chambers 26 when the fitting plate 46 is opened to its unfolded planar operative configuration as best seen in FIGS. 3 and 4. This open configuration provides full open area flow into the pneumatic flow chambers 26 through the port 42 and provides for easy nozzle 38 insertion into the blanket 10 edge 32.

As seen in FIG. 3, the fitting plate 46 preferably contains explanatory labeling to assist the user in the proper use of the invention and provides for simultaneous labeling of the blanket upper and bottom surfaces without additional labels. The plate first end extension 56 and second end extension 58 are labeled with the words "INLET" to mark the port 42 location into which the conditioned supply air is introduced. On the circular center portion 52, the plate first end 48 to which the upper sheet 12 is attached is identified by the words "THIS SIDE UP", and the plate second end 50 to which the blanket lower surface 22 is attached is identified by the words "THIS SIDE DOWN". Intermediate the plate first end 48 and second end 50 on the center portion 52 is a fold line 60 identified by dashed lines across the fitting plate central portion 52. This fold line is aligned with the blanket edge 32 when the fitting plate 46 is installed on the blanket 10.

Semicircular cuts are made in the blanket upper sheet and lower sheet first ends 34 as seen in FIG. 1, which define the blanket chamber port 42 at which the fitting plate 46 is mounted as in FIG. 1. The plate 46 is aligned with the upper sheet 12 and the laminated assembly 18 and installed in line with the blanket edge 32 forming a hinge-like relationship with the blanket edge 32 as seen in FIG. 5. Because the adhesive is applied only to the plate center portion 52 inner side 62, forming a bond 64, the end extensions are free of the blanket surfaces. By remaining free, the inflated blanket profile and stress to the adhesive bond 64 during inflation are minimized; and the plate first end extension 56 and the plate second end extension 58 may be grasped and separated during nozzle insertion. As shown in FIG. 5, the fitting plate 46 provides concise packaging because it compactly folds along the plate fold line 60 providing a low profile; this configuration has the further advantage of reducing the stress to the interface bond 64 during storage and packaging.

The external conditioned air supply, not shown, can be a separate heating or cooling/dehumidification unit or a unified system and forms no part of the invention. The air supplies are typically transportable low pressure units, similar to a hair dryer construction or the like, having a moderate volume flow rate for which the orifices 20 are sized. The air supply is connected to the blanket by means of the flexible hose 44 as described below.

The pneumatic blanket 10 is typically used to adjust or maintain patient body temperatures through the application of either warming or cooling air for surgical, post operative, hypothermic or hyperthermic patients. In use, pneumatic blanket 10 is fully opened and positioned to cover the body area to be treated; if the whole body is to be covered, then the blanket is positioned lengthwise over the patient with the fitting plate 46 adjacent the patient's feet. Next, the fitting plate 46, which has been folded during storage, is grasped with appropriate fingers behind the extensions 56 and 58 and the thumb or thumbs are positioned at the plate fold line 60 on the outer surface of the plate. By pressing inwardly on the plate fold line 60 while separating extensions 56 and 58 the fitting plate may be opened to a substantially vertical planar configuration as shown in FIG. 4. Next, while maintaining pressure on the fitting plate 46 such that it is in the open, planar configuration the air supply nozzle 38 is inserted into the fitting plate central opening 54 until a snug sealed fit between the plate 46 and the nozzle 38 is obtained as in FIG. 4. Of course, the size of the nozzle 38 and opening 54 are such that the nozzle will tightly wedge into the opening 54 to form an effective seal. Conditioned air may now be supplied to the nozzle which will inflate the blanket and cause the air within the blanket 10 to be exhausted through the blanket orifices 20 in the blanket bottom. By bathing the patient in a constant, gentle flow of air the desired body temperature effect may be achieved without the tissue damage or discomfort often caused by indirect or direct contact with a heat exchanging member.

It is appreciated that various modifications to the inventive concepts may be apparent to those skilled in the art without departing from the spirit and scope of the invention.

We claim:

1. A pneumatic, disposable, temperature control blanket receiving conditioned air though an external air supply connection means, comprising, in combination, an upper thermoplastic air impervious flexible sheet and a lower thermoplastic flexible sheet each having a first end, an opposing second end and edges defining a periphery, said first end lower flexible sheet being adjacent said first end upper flexible sheet, said lower sheet having a lower bottom surface, a heat seal bonding said upper flexible sheet periphery to said lower flexible sheet periphery, a pneumatic flow chamber defined by said sheets, said upper flexible sheet being heat sealed to said lower flexible sheet at a multitude of staking points distributed in a staggered pattern within said sheets' peripheral edges thereby defining redundant multiple air flow paths within said pneumatic flow chamber, an inlet air port defined in said pneumatic flow chamber, an inlet air connection means affixed to said sheets in communication with said inlet air port adapted to receive the inlet air supply connection means to inflate said pneumatic flow chamber, an outer fibrous bottom lamina material bonded to said lower flexible sheet bottom surface thereby comprising a lower laminated assembly to provide a slide resistant comfortable patient contact surface, an outwardly disposed air flow orifice array defined in said laminated assembly in communication with said pneumatic flow chamber to convey temperature controlled air from said pneumatic flow chamber to the patient, said orifice array comprising a plurality of substantially evenly spaced openings defined in said laminated assembly sized to maintain a predetermined pneumatic flow chamber pressure over a range of predetermined air source volume flow rates.

2. A pneumatic, disposable, temperature control blanket as in claim 1, wherein said inlet air connection means comprises a folding plate affixed to said sheets adjacent said edges thereof defining an opening in communication with said inlet air port adapted to receive the air supply connection means.

3. A pneumatic, disposable, temperature control blanket receiving conditioned air through an external air supply connection means, comprising, in combination, an upper flexible sheet and a lower flexible sheet each having a first end, an opposing second end and edges defining a periphery, said first end lower flexible sheet being adjacent said first end upper flexible sheet, a peripheral bonding means bonding said upper flexible sheet periphery to said lower flexible sheet periphery, a pneumatic flow chamber defined by said sheets having walls, an inlet air port defined in said pneumatic flow chamber, an inlet air connection means affixed to said sheets in communication with said inlet air port adapted to receive the inlet air supply connection means to inflate said pneumatic flow chamber, an outer fibrous bottom lamina material bonded to said lower flexible sheet thereby comprising a laminated assembly to provide a slide resistant comfortable patient contact surface, an outwardly disposed air flow orifice array defined in said laminated assembly in communication with said pneumatic flow chamber to convey temperature controlled air from said pneumatic flow chamber to the patient, said orifice array comprising a plurality of openings sized to maintain pneumatic flow chamber pressure over a range of air source volume flow rates, said inlet connection means comprising an articulating fitting plate having a folded mode and an unfolded inflation mode, an opening defined in said fitting plate in communication with said port adapted to sealingly receive the air supply connection means when said plate is in said unfolded mode, said fitting plate being attached to said upper flexible sheet first end and said lower flexible sheet first end, said inlet air port and fitting plate being located intermediate said upper and lower flexible sheets at said sheet's edges to permit the introduction of supply air in said chamber in the direction of the general plane of the blanket minimizing flow restrictions.

4. A pneumatic, disposable, temperature control blanket for receiving conditioned air through an external air supply nozzle, comprising, in combination, a substantially planar chamber having a flexible upper wall, a flexible lower wall and an edge, a port communicating with said chamber defined in said edge, a folding fitting plate affixed to said upper and lower walls having a central opening in communication with said port, said fitting plate having a fold line in alignment with said chamber edge, said fitting plate central opening adapted to slidingly, sealingly receive the air supply nozzle in the blanket plane upon said plate being unfolded, an orifice array defined in said lower chamber wall, said orifices being in communication with said chamber outwardly disposed to discharge chamber air onto the patient.

5. A pneumatic, disposable, temperature control blanket as in claim 4, wherein said fitting plate comprises an elongated member having a first end defining a first end extension, a second end defining a second end extension and a circular portion intermediate said first and second ends, said circular portion having a central opening defined therein in alignment with said port, adapted to receive the air supply nozzle.

6. A pneumatic, disposable, temperature control blanket as in claim 5, wherein said fitting plate circular portion only is sealingly bonded to said flexible upper wall and said flexible lower wall at said blanket edge thereby leaving said plate extensions free to move relative said blanket, said circular portion central opening adapted to align and communicate with said port.

7. A pneumatic, disposable, temperature control blanket as in claim 5, wherein said fitting plate is fabricated of a flexible, foldable material with an outer surface adapted to receive indicia thereon.

8. A pneumatic, disposable, temperature control blanket as in claim 7, indicia located on said fitting plate outer surface for explanatory and orientation purposes.

9. A pneumatic, disposable, temperature control blanket as in claim 7, wherein said fitting plate material is cardboard.

* * * * *